(12) United States Patent
Ishida et al.

(10) Patent No.: US 7,241,915 B2
(45) Date of Patent: Jul. 10, 2007

(54) PROCESS FOR INHIBITION OF POLYMERIZATION OF (METH)ACRYLATE ESTER

(75) Inventors: Tokumasa Ishida, Himeji (JP); Yasuhiro Shingai, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 724 days.

(21) Appl. No.: 10/361,973

(22) Filed: Feb. 11, 2003

(65) Prior Publication Data

US 2003/0176725 A1    Sep. 18, 2003

(30) Foreign Application Priority Data

Mar. 12, 2002    (JP)    ............... 2002-067544

(51) Int. Cl.
  *C07C 67/27*    (2006.01)
  *C07C 69/533*    (2006.01)
(52) U.S. Cl. ...................... 560/209; 560/205
(58) Field of Classification Search ................. 560/205
  See application file for complete search history.

(56) References Cited

U.S. PATENT DOCUMENTS 5,262,569 A    11/1993    Upmacis et al.
5,292,920 A    3/1994    Upmacis et al.
5,504,243 A *  4/1996    Sakamoto et al. .......... 560/205
6,329,543 B1 * 12/2001   Knebel et al. .............. 560/220
6,849,758 B1   2/2005    Muller-Engel et al.

FOREIGN PATENT DOCUMENTS

| DE | 199 47 868 A1 | 4/2001 |
|----|---------------|--------|
| EP | 0 685 447 A2  | 12/1995 |
| JP | 58-46496 B2   | 10/1983 |
| JP | 5-194346 A    | 8/1993 |
| JP | 2725638 B2    | 12/1997 |
| JP | 10-237022 A   | 9/1998 |
| JP | 2001-348362 A | 12/2001 |
| WO | WO 01/25173 A1 | 4/2001 |

* cited by examiner

*Primary Examiner*—Johann Richter
*Assistant Examiner*—Yevgeny Valenrod

(57) ABSTRACT

The present invention provides a process for inhibition of polymerization of a (meth)acrylate ester, which has an extremely higher effect of inhibition of polymerization than in cases where conventional polymerization inhibitors are used. In the process for inhibition of polymerization of a (meth)acrylate ester; an N-oxyl compound and at least one member selected from the group consisting of manganese salt compounds, copper salt compounds, 2,2,6,6-tetramethylpiperidine compounds, and nitroso compounds are used together as polymerization inhibitors, and further an acid is used.

6 Claims, No Drawings

PROCESS FOR INHIBITION OF POLYMERIZATION OF (METH)ACRYLATE ESTER

BACKGROUND OF THE INVENTION

A. Technical Field

The present invention relates to a process for inhibition of polymerization of a (meth)acrylate ester.

B. Background Art

In a process in which the reaction between (meth)acrylic acid and an alkylene oxide is carried out in the presence of a catalyst in order to produce a hydroxyalkyl (meth)acrylate, both the (meth)acrylic acid as a raw material and the hydroxyalkyl (meth)acrylate as the objective product have so polymerizable an unsaturated group as to easily polymerize due to such as light and heat. Therefore, it is important to inhibit their polymerization. General methods therefor involve using polymerization inhibitors, and the use of various polymerization inhibitors is attempted. Known as specific examples thereof are methods that involve using such as N-oxyl compounds and nitroso compounds. For example, JP-B-046496/1983 discloses a method that involves using an N-oxyl compound (e.g. 2,2,5,5-tetramethyl-3-oxopyrrolidine-1-oxyl and 2,2,6,6-tetramethyl-4-acetoxypiperidine-1-oxyl) as a polymerization inhibitor in order to inhibit the polymerization of α,β-unsaturated carboxylate esters. In addition, JP-A-194346/1993 discloses a method that involves using an N-nitroso-N-phenyl-N-hydroxylamine salt as a polymerization inhibitor in order to inhibit the polymerization of unsaturated monomers such as acrylic acid and esters thereof. Furthermore, Japanese Patent No. 2725638 proposes a method that involves using, together with the N-oxyl compound, at least one member selected from the group consisting of manganese salt compounds, copper salt compounds, 2,2,6,6-tetramethylpiperidine compounds, and nitroso compounds as polymerization inhibitors in order to inhibit the polymerization of (meth)acrylic acid and esters thereof.

However, even if these conventional polymerization inhibitors are added, there occur problems such that: while the hydroxyalkyl (meth)acrylate is distilled, a polymerized product is formed to result in the impossibility of the long-term operation of a production apparatus including a distillation column. Therefore, their effect of inhibition of polymerization has not been sufficient.

SUMMARY OF THE INVENTION

A. Object of the Invention

An object of the present invention is to provide a process for inhibition of polymerization of a (meth)acrylate ester, which has an extremely higher effect of inhibition of polymerization than in cases where conventional polymerization inhibitors are used.

B. Disclosure of the Invention

The present inventors have diligently studied in order to solve the above-mentioned problems. As a result, they have found out that surprisingly, the above problems can be solved by: using an N-oxyl compound and at least one member selected from the group consisting of manganese salt compounds, copper salt compounds, 2,2,6,6-tetramethylpiperidine compounds, and nitroso compounds together as polymerization inhibitors, and further using an acid.

That is to say, in the process for inhibition of polymerization of a (meth)acrylate ester, according to the present invention; an N-oxyl compound and at least one member selected from the group consisting of manganese salt compounds, copper salt compounds, 2,2,6,6-tetramethylpiperidine compounds, and nitroso compounds are used together as polymerization inhibitors, and further an acid is used. These and other objects and the advantages of the present invention will be more fully apparent from the following detailed disclosure.

DETAILED DESCRIPTION OF THE INVENTION

Although there is no especial limitation on the (meth)acrylate ester to which the present invention process for inhibition of polymerization is applicable, yet examples thereof include: acrylate esters, such as methyl acrylate, ethyl acrylate, butyl acrylate, 2-ethylhexyl acrylate, and hydroxyalkyl acrylates; and methacrylate esters, such as methyl methacrylate, butyl methacrylate, and hydroxyalkyl methacrylates.

First of all explained is the outline of a production process for the hydroxyalkyl (meth)acrylate, to which the present invention process for inhibition of polymerization is favorably applicable.

At first, the addition reaction between (meth)acrylic acid and an alkylene oxide is carried out in the presence of a catalyst. The conversion of this addition reaction is frequently less than 100%, and therefore it is general that such as unreacted (meth)acrylic acid and unreacted alkylene oxide remain in the resultant reaction liquid at the end of the reaction. Therefore, after the end of the reaction, the above reaction liquid is led to a step for removing such as these unreacted raw materials from the reaction liquid. Then, as the subsequent final step, the purification is carried out by such as distillation, thus obtaining the objective hydroxyalkyl (meth)acrylate.

Hereinafter explained is a step of the addition reaction between the (meth)acrylic acid and the alkylene oxide in the presence of the catalyst.

As to the amounts of the raw materials as charged for the above reaction between the (meth)acrylic acid and the alkylene oxide in preparation for the implementation of the present invention, the amount of the alkylene oxide is favorably not smaller than 1 mol, more favorably in the range of 1.0 to 10.0 mols, still more favorably 1.0 to 5.0 mols, yet still more favorably 1.0 to 3.0 mols, particularly favorably 1.0 to 2.0 moles, relative to 1 mol of the (meth)acrylic acid. In the case where the amount of the alkylene oxide as charged is smaller than 1.0 mol, there are disadvantages in that: the conversion is lowered, and by-products are increased. In addition, in the case where the amount of the alkylene oxide as charged is too large, particularly, larger than 10 mols, there are economical disadvantages in that there is a case where a recovery step is necessary.

Although there is no especial limitation on the alkylene oxide that is usable in the present invention, yet the alkylene oxide is favorably an alkylene oxide having 2 to 6 carbon atoms, more favorably having 2 to 4 carbon atoms. Examples thereof include ethylene oxide, propylene oxide, and butylene oxide. The ethylene oxide and the propylene oxide are favorable.

In the present invention, the reaction between the (meth)acrylic acid and the alkylene oxide in the presence of the catalyst can be carried out according to methods as generally used in this kind of reaction.

For example, in the case of carrying out the reaction in a batchwise manner, the reaction is carried out by introducing a liquid alkylene oxide into the (meth)acrylic acid. In the case where the (meth)acrylic acid is solid, the alkylene oxide may be introduced after the unsaturated carboxylic acid has been dissolved into a solvent. Hereupon, the alkylene oxide may be added in a lump or continuously or intermittently. Then, in the case where the alkylene oxide is added continuously or intermittently, as is often carried out in this kind of reaction, it is permissible that: the reaction is continued still after the introduction of the alkylene oxide, thus carrying out what is called aging to complete the reaction. In addition, it is not always necessary to charge the (meth)acrylic acid all at once in the initial stage, but it is permissible to add the (meth)acrylic acid one by one in the form divided into several portions.

In addition, in the case of carrying out the reaction in a continuous manner, the reaction is carried out by continuously charging the (meth)acrylic acid and a liquid alkylene oxide into such as a tubular or tank-type reactor and continuously extracting the resultant reaction liquid from the reactor. Hereupon, the catalyst may be continuously supplied together with the raw materials and continuously extracted together with the reaction liquid. In the case of such as the tubular reactor, the catalyst may be used in what is called a fixed-bed manner such that a solid catalyst is used in the form packed in the reactor. In addition, in the case of such as the tank-type reactor, the catalyst may be used in what is called a fluidized-bed manner such that a solid catalyst is used in the form fluidized together with the reaction liquid in the reactor. In addition, in the cases of these continuous reactions, there may be adopted a mode that a portion of the reaction liquid is circulated.

As to the addition of the raw (meth)acrylic acid and the raw alkylene oxide into the reactor, they may be added from different addition lines, or they may be added after having beforehand been mixed by using such as piping, a line mixer, or a mixing tank before being added to the reactor. In addition, in the case where a liquid as discharged from an outlet of the reactor is circulated to an inlet of the reactor, or in the case where the unreacted alkylene oxide and the unreacted (meth)acrylic acid are recovered and reused, these liquids may be added to the reactor after having been mixed with the raw (meth)acrylic acid and the raw alkylene oxide. However, in the case where the (meth)acrylic acid and the alkylene oxide are added from the different addition lines to the reactor, the molar ratio of the (meth)acrylic acid in the reaction liquid is excessive in the neighborhood of an addition inlet of the (meth)acrylic acid, therefore it is favorable that the raw materials may be added after having beforehand been mixed together by using such as piping before being added to the reactor.

The reaction is usually carried out in the reaction temperature range of favorably 40 to 130° C., more favorably 50 to 100° C. In the case where the reaction temperature is lower than 40° C., the proceeding of the reaction is so slow as to deviate from a practical use level. On the other hand, in the case where the reaction temperature is higher than 130° C., there are disadvantages in that: by-products are increased, or there occur such as polymerizations of the (meth)acrylic acid as a raw material and of the hydroxyalkyl (meth)acrylate as the objective product.

In addition, for the purpose of such as getting the reaction to mildly proceed in this reaction, the reaction may be carried out in a solvent. Usable as the solvent are general solvents such as toluene, xylene, heptane, and octane. The pressure in the system during the reaction depends upon the kinds and mixing ratios of the raw materials as used, but generally the reaction is carried out under increased pressure.

In the present invention, the unreacted alkylene oxide and/or the unreacted (meth)acrylic acid may be recovered and reused as the raw reaction materials for the hydroxyalkyl (meth)acrylate. In this way, the reduction of production costs can be achieved still more by reusing the recovered unreacted raw materials as the raw reaction materials. Incidentally, the recovered unreacted raw materials may contain the hydroxyalkyl (meth)acrylate. In addition, the hydroxyalkyl (meth)acrylate may be added to the reactor after having been mixed with the recovered raw materials in view of controlling the heat of the reaction as generated. However, when the amount of the hydroxyalkyl (meth)acrylate as added to the reactor increases, the amounts of formed by-products such as diesters increase. Therefore, the amount of the hydroxyalkyl (meth)acrylate as contained in the recovered raw materials is favorably not larger than 4.0 times, more favorably not larger than 2.0 times, still more favorably not larger than 1.0 time, based on the weight relative to the total amount of the recovered raw acid and the raw acid as freshly added.

In the present invention, there is no especial limitation on the catalyst as used in the reaction between the (meth)acrylic acid and the alkylene oxide, and usable are catalysts as generally used in this kind of reaction. Specifically, favorably usable is at least one member selected from the group consisting of: chromium compounds, such as chromium chloride, chromium acetylacetonate, chromium formate, chromium acetate, chromium acrylate, chromium methacrylate, sodium bichromate, and chromium dibutyldithiocarbamate; iron compounds, such as iron powders, iron chloride, iron formate, iron acetate, iron acrylate, and iron methacrylate; and amine compounds, such as trialkylamines, cyclic amines (e.g. pyridine), their quaternary salts, and resins having basic functional groups (e.g. tertiary amino groups, quaternary ammonium salts, and pyridinium groups).

There is no especial limitation on the amount of the above catalyst as used for carrying out the present invention. In the case where the batchwise reaction is carried out by using a heterogeneous catalyst, the catalyst is usually used in an amount of 5 to 50 weight %, favorably 10 to 30 weight %, of the raw (meth)acrylic acid. In the case where the catalyst is used in the fluidized-bed manner with such as the tank-type reactor in the continuous reaction, the catalyst is usually used in the range of 30 to 90 vol %, favorably 50 to 80 vol %, of the volume of the reaction liquid. In addition, in the case where the catalyst is used in the fixed-bed manner with such as the tubular reactor, a liquid containing the raw reaction materials is favorably passed through the reactor at a liquid space velocity (LHSV: $h^{-1}$) of 0.05 to 15, more favorably 0.2 to 8. On the other hand, in the case of a homogeneous catalyst, the catalyst is usually used in amount of 0.05 to 10 weight %, favorably 0 1 to 3 weight %.

In the present invention, the crude hydroxyalkyl (meth)acrylate as obtained may further be purified when the occasion demands. Although there is no especial limitation on the purification method, yet examples thereof include purification by distillation. More particularly, specific examples thereof include distillation by using such as: distillation columns (as widely used) and rectifying columns (e.g. packed columns, bubble-cap columns, perforated-plate columns), but there is no especial limitation thereto. In addition, other purification means may be used together with the purification by the distillation. The purification by the distillation can be carried out under conditions as generally used for the distillation of the hydroxyalkyl (meth)acrylate. Specifically, the distillation is carried out, for example, at a temperature of 50 to 120° C. (favorably 60 to 100° C.) under a pressure of 1 to 10 hPa (favorably 2 to 7 hPa). Incidentally, as is mentioned below, in the present invention, there is used an acid having an effect of suppressing the formation of diesters. However, if the unreacted alkylene oxide remains during the distillation, this alkylene oxide reacts with the acid, thereby lowering the effect of suppressing the formation of diesters. Therefore, favorably for avoiding this matter, the crude hydroxyalkyl (meth)acrylate is subjected to the distillation after the residual unreacted alkylene oxide has been removed under reduced pressure.

In the present invention, the N-oxyl compound and the at least one member selected from the group consisting of manganese salt compounds, copper salt compounds, 2,2,6,6-tetramethylpiperidine compounds, and nitroso compounds are used together as polymerization inhibitors.

Although there is no especial limitation on the manganese salt compounds, yet examples thereof include manganese dialkyldithiocarbamates (wherein the alkyl groups are any ones of a methyl group, an ethyl group, a propyl group, and a butyl group, and may be either identical with or different from each other), manganese diphenyldithiocarbamate, manganese formate, manganese acetate, manganese octanoate, manganese naphthenate, manganese permanganate, and manganese ethylenediaminetetraacetate. The manganese salt compounds may be used either alone respectively or in combinations with each other.

Although there is no especial limitation on the copper salt compounds, yet examples thereof include copper dialkyldithiocarbamates (wherein the alkyl groups are any ones of a methyl group, an ethyl group, a propyl group, and a butyl group, and may be either identical with or different from each other) and copper diphenyldithiocarbamate. The copper salt compounds may be used either alone respectively or in combinations with each other.

Although there is no especial limitation on the 2,2,6,6-tetramethylpiperidine compounds, yet examples thereof include 2,2,6,6-tetramethylpiperidine, 4-hydroxy-2,2,6,6-tetramethylpiperidine, 1-hydroxy-2,2,6,6-tetramethylpiperidine, and 1,4-dihydroxy-2,2,6,6-tetramethylpiperidine. The 2,2,6,6-tetramethylpiperidine compounds may be used either alone respectively or in combinations with each other.

Although there is no especial limitation on the nitroso compounds, yet examples thereof include nitrosophenol, N-nitrosodiphenylamine, isoamyl nitrite, N-nitroso-cyclohexylhydroxylamine, N-nitroso-N-phenylhydroxylamine, and their salts. The nitroso compounds may be used either alone respectively or in combinations with each other.

Although there is no especial limitation on the N-oxyl compound, yet examples thereof include 2,2,4,4-tetramethylazetidine-1-oxyl, 2,2-dimethyl-4,4-dipropylazetidine-1-oxyl, 2,2,5,5-tetramethylpyrrolidine-1-oxyl, 2,2,5,5-tetramethyl-3-oxopyrrolidine-1-oxyl, 2,2,6,6-tetramethylpiperidine-1-oxyl, 4-hydroxy-2,2,6,6-tetramethylpiperidine-1-oxyl, 6-aza-7,7-dimethyl-spiro(4,5)decane-6-oxyl, 2,2,6,6-tetramethyl-4-acetoxypiperidine-1-oxyl, 2,2,6,6-tetramethyl-4-benzoyloxypiperidine-1-oxyl, and 4,4',4''-tris-(2,2,6,6-tetramethylpiperidine-1-oxyl) phosphite. The N-oxyl compounds may be used either alone respectively or in combinations with each other.

In the present invention, the N-oxyl compound and the at least one member selected from the group consisting of the manganese salt compounds, the copper salt compounds, the 2,2,6,6-tetramethylpiperidine compounds, and the nitroso compounds are used together as the polymerization inhibitors, but other polymerization inhibitors may be used together with these polymerization inhibitors when the occasion demands. There is no especial limitation on such other polymerization inhibitors, and usable are publicly known polymerization inhibitors as generally used. Specific examples thereof include: phenol compounds, such as hydroquinone, methylhydroquinone, tert-butylhydroquinone, 2,6-di-tert-butylhydroquinone, 2,5-di-tert-butylhydroquinone, 2,4-dimethyl-6-tert-butylphenol, hydroquinone monomethyl ether, cresol, and tert-butylcatechol; p-phenylenediamines, such as N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N,N'-diphenyl-p-phenylenediamine, and N,N'-di-2-naphthyl-p-phenylenediamine; amine compounds, such as thiodiphenylamime and phenothiazine; tetraalkylthiuram disulfides, such as tetrabutylthiuram disulfide, tetrapropylthiuram disulfide, tetraethylthiuram disulfide, and tetramethylthiuram disulfide; and Methylene Blue. These other polymerization inhibitors may be used either alone respectively or in combinations with each other.

In addition, the effect of inhibition of polymerization is further enhanced if molecular oxygen is further used together when the occasion demands.

The amount of the polymerization inhibitors as used is fitly adjusted according to such as operational conditions, and it is not especially limited. However, the total amount of the polymerization inhibitors as used is favorably in the range of 0.00001 to 1 weight %, more favorably 0.00005 to 0.1 weight %, still more favorably 0.0001 to 0.05 weight %, of the (meth)acrylate ester. As to the amounts of the individual polymerization inhibitors as used, the N-oxyl compound is used in an amount of favorably 0.00001 to 0.5 weight %, more favorably 0.00005 to 0.1 weight %, still more favorably 0.0001 to 0.05 weight %, of the (meth)acrylate ester. The manganese salt compound is used in an amount of favorably 0.00001 to 0.5 weight %, more favorably 0.00005 to 0.1 weight %, still more favorably 0.0001 to 0.05 weight %, of the (meth)acrylate ester. The copper salt compound is used in an amount of favorably 0.00001 to 0.5 weight %, more favorably 0.00005 to 0.1 weight %, still more favorably 0.0001 to 0.05 weight %, of the (meth)acrylate ester. The 2,2,6,6-tetramethylpiperidine compound is used in an amount of favorably 0.00001 to 0.5 weight %, more favorably 0.00005 to 0.1 weight %, still more favorably 0.0001 to 0.05 weight %, of the (meth)acrylate ester. The nitroso compound is used in an amount of favorably 0.00001 to 0.5 weight %, more favorably 0.00005 to 0.1 weight %, still more favorably 0.0001 to 0.05 weight %, of the (meth)acrylate ester. In the case where the amount of the polymerization inhibitors as used is smaller than the above range, it tends to be impossible to sufficiently obtain the effect of inhibition of polymerization. In addition, in the case where the amount is larger than the above range, there are disadvantages of being uneconomical.

As long as the polymerization inhibitors are added in such a manner that the polymerization of the (meth)acrylate ester can be inhibited, the polymerization inhibitors can be added, in any mode and by any method, to any place of all the steps of the production process for the (meth)acrylate ester. The polymerization inhibitors may be added in such a manner that the polymerization inhibitors can coexist with the (meth)acrylic eater in any step in which the polymerization tends to occur, favorably in such as a reaction step, an aging step, and a distillation step, more favorably in such as a distillation step, still more favorably in a distillation step after the residual unreacted alkylene oxide has been removed, yet still more favorably in a distillation step after the residual unreacted (meth)acrylic acid and alkylene oxide have been removed.

In the present invention, there is used the acid together with the above polymerization inhibitors.

Although there is no especial limitation on the acid, yet examples thereof include: carboxylic acids and carboxylic anhydrides, such as oxalic acid, oxalic anhydride, malonic acid, succinic acid, succinic anhydride, fumaric acid, maleic acid, maleic anhydride, octanoic acid, adipic acid, sebacic acid, tetradecanedicarboxylic acid, 1,2,4-butanetricarboxylic acid, 1,3,6-hexanetricarboxylic acid, 1,2,3,4-butanetetracarboxylic acid, 1,2,3,4-pentanetetracarboxylic acid, 1,6,7,12-dodecanetetracarboxylic acid, benzoic acid, o-toluic acid, m-toluic acid, p-toluic acid, phthalic acid, phthalic anhydride, isophthalic acid, terephthalic acid, 2,6-naphthalenedicarboxylic acid, pyromellitic acid, pyromellitic anhydride, 1,2,4-benzenetricarboxylic acid, 1,4,5,8-naphthalenetetracarboxylic acid, 1,3,5,7-naphthalenetetracarboxylic acid, poly(meth)acrylic acid, salicylic acid, and acetic acid. These may be used either alone respectively or in combinations with each other.

The acid may be added in a lump, but the acid is favorably added one by one in the form divided into at least two portions. When the acid is added in a lump in the reaction step, there is a possibility that the acid may be consumed, for example, by partially or entirely reacting with the alkylene oxide. Also, this acid has the effect of suppressing the formation of diesters, and therefore there is a possibility that this effect may be lost (deactivated) by the consumption of the acid. Accordingly, for preventing or suppressing the formation of diesters in the reaction step by adding the acid, it is necessary to add a large amount of the acid in consideration of a deactivated portion of the acid. However, when the large amount is added, the behavior and state of a distillation bottom liquid are deteriorated in the distillation step. In addition, when the acid is added in a lump in the distillation step, the formation of diesters cannot be prevented or suppressed in the reaction step. In addition, the deactivation of the acid is promoted by thermal hysteresis in the production process for the (meth)acrylate ester. Thus, if the acid is added one by one in the form divided into at least two portions, the deactivation can be suppressed to an extremely low level, because the total thermal hysteresis of the acid is shortened. Therefore, the loss of the acid is reduced in the steps, so the amount of the acid as added can be decreased. As a result, a high-quality (meth)acrylate ester having a still lower diester content can be produced without causing the above problem such that the behavior and state of the distillation bottom liquid are deteriorated in the distillation step.

When the acid is added one by one in the form divided into at least two portions, there is no especial limitation on the number of the divided portions. However, the acid is favorably added one by one in the form divided into 2 to 10 portions, particularly favorably 3 portions, in consideration of such as workability.

Examples of representative addition methods in which the acid is added one by one in the form divided into two portions (in the case of the reaction between the (meth)acrylic acid and the alkylene oxide) are enumerated below. Incidentally, hereinafter the terms "before the reaction" and "starting raw materials" mean "before the alkylene oxide is introduced" and "(meth)acrylic acid (that may include such as catalyst and polymerization inhibitor)" respectively.

(1) A portion of the acid is added to the starting raw material before the reaction, and the rest is added to the reaction liquid during the reaction.

(2) A portion of the acid is added to the starting raw material before the reaction, and the rest is added in the stage of aging the reaction liquid.

(3) A portion of the acid is added to the starting raw material before the reaction, and the rest is added before the resultant reaction product is distilled.

(4) A portion of the acid is added to the reaction liquid during the reaction, and the rest is added in the stage of aging the reaction liquid.

(5) A portion of the acid is added to the reaction liquid during the reaction, and the rest is added before the resultant reaction product is distilled.

(6) A portion of the acid is added in the stage of aging the reaction liquid, and the rest is added before the resultant reaction product is distilled.

Of these methods (1) to (6), those in which a portion of the acid is added to the starting raw material before the reaction to thereby arrange that the acid should exist in the reaction liquid from the beginning of the reaction are favorable in view of effectively preventing or suppressing the side-formation of diesters, and the method (3) is particularly favorably used.

Examples of representative addition methods in which the acid is added one by one in the form divided into three portions are enumerated below.

(7) A portion of the acid is added to the starting raw material before the reaction, and the rest is added during the reaction and in the stage of aging the reaction liquid.

(8) A portion of the acid is added to the starting raw material before the reaction, and the rest is added during the reaction and before the resultant reaction product is distilled.

(9) A portion of the acid is added to the starting raw material before the reaction, and the rest is added in the stage of aging the reaction liquid and before the resultant reaction product is distilled.

(10) A portion of the acid is added to the reaction liquid during the reaction, and the rest is added in the stage of aging the reaction liquid and before the resultant reaction product is distilled.

Of these methods (7) to (10), the method (9) is favorably used.

Incidentally, the method for the divided additions of the acid is not limited to the above methods (1) to (10). As long as the acid is added one by one in the form divided into at least two portions (particularly favorably three portions) in a manner such that the total thermal hysteresis will be shortened, the acid can be added to any place of all the steps of the production process for the (meth)acrylate ester.

Although there is no especial limitation on the total amount of the acid as added, yet this total amount is favorably in the range of 0.0001 to 1 weight %, more favorably 0.001 to 1 weight %, still more favorably 0.005 to 0.5 weight %, relative to the (meth)acrylate ester. In the case where the total amount of the acid as added is smaller than 0.0001 weight % relative to the (meth)acrylate ester, there are disadvantages in that: it tends to be impossible to sufficiently obtain the effect of inhibition of polymerization, and also it tends to be impossible to effectively suppress the formation of diesters. In addition, in the case where the total amount of the acid as added is larger than 1 weight %, there are disadvantages in that there is a tendency to easily cause the deterioration of the behavior and state of the distillation bottom liquid in the distillation step.

Incidentally, in the case of adding the acid one by one in the form divided into at least two portions, the amount of the acid as added to each place to which the addition is to be made should be determined in such a range that at least the effect of the acid can be obtained. This range depends upon the kind of the acid, and therefore it cannot be specified sweepingly. However, the amount is usually in the range of favorably 0.0001 to 1 weight %, more favorably 0.001 to 1 weight %, still more favorably 0.005 to 0.5 weight %, relative to the (meth)acrylate ester.

In the case of carrying out the reaction between the (meth)acrylic acid and the alkylene oxide, there is no especial limitation on the alkylene oxide concentration in the reaction liquid. However, when the alkylene oxide concentration increases, the deactivation of the acid is easily caused, and the side-formation of the diesters cannot effectively be prevented or suppressed. Therefore, it is good that the reaction is carried out while the alkylene oxide concentration in the reaction liquid is maintained in the range of favorably not larger than 10 weight %, more favorably 0.1 to 10 weight %, more favorably 0.1 to 5 weight %.

In addition, in the case of adding the acid after the alkylene oxide has been added to the (meth)acrylic acid, it is, for the same reasons as the above, good that the acid is added either after the alkylene oxide concentration in the reaction liquid has decreased to favorably not larger than 10 weight %, more favorably not larger than 5 weight %, still more favorably not larger than 3 weight %, with the passage of the reaction or after the alkylene oxide concentration in the reaction liquid has been adjusted to favorably not larger than 10 weight, more favorably not larger than 5 weight %, still more favorably not larger than 3 weight %, by adding a solvent inactive to the reaction (e.g. pentane, hexane, heptane, octane, acetone, methyl isobutyl ketone, ethyl acetate, tetrahydrofuran, benzene, toluene, and xylene).

Also by such a reason, it is good that: as is mentioned above, the acid is added to the starting raw material before the beginning of the reaction, and thereafter the reaction is carried out while the alkylene oxide concentration in the reaction liquid is maintained in the range of favorably not larger than 10 weight %, more favorably 0.1 to 10 weight %, more favorably 0.1 to 5 weight %.

In order to maintain the alkylene oxide concentration in the range of not larger than 10 weight % in the reaction liquid in the above method, for example, the liquid alkylene oxide may be introduced into the starting raw material little by little continuously or intermittently.

Accordingly, in the present invention, it is particularly favorable that the reaction is carried out while the alkylene oxide concentration in the reaction liquid is maintained in the range of not larger than 10 weight % in the aforementioned methods (1) to (3) and (7) to (9) (particularly in the methods (7) to (9)). Also, a still-higher-quality hydroxyalkyl ester having a still lower diester content can be obtained by distilling the reaction product as obtained in the above way.

In addition, the deterioration of the behavior and state of the distillation bottom liquid during the distillation can also be prevented effectively, because the total amount of the acid as used can be decreased.

Effects and Advantages of the Invention

In a production process for a (meth)acrylate ester, the present invention process can sufficiently prevent the polymerizations of the (meth)acrylic acid as a raw material and of the (meth)acrylate ester as the objective product, and further can sufficiently suppress the formation of diesters.

DETAILED DESCRIPTION OF THE PREFERRED EMBODIMENTS

Hereinafter, the present invention is more specifically illustrated by the following examples of some preferred embodiments in comparison with comparative examples not according to the invention. However, the present invention is not limited to the following examples. Incidentally, the hydroxyethyl acrylate as used in the examples was that from which the stabilizer had been removed by purification.

Example 1

A glass-made container was charged with 100 g of hydroxyethyl acrylate, and then thereto 0.002 g of 4-hydroxy-2,2,6,6-tetramethylpiperidine-1-oxyl (0.002 weight %), 0.002 g of manganese acetate (0.002 weight %), and 0.1 g of maleic acid (0.1 weight %) were further added. Subsequently, the pressure in the glass-made container was reduced to 4 hPa, and immediately thereafter the glass-made container was immersed into an oil bath as adjusted to 80° C., and how long time passed until a polymerized product formed was checked with the eye. As a result, after 2.5 hours had passed, the polymerized product began to form. The result is listed in Table 1.

Examples 2 to 13

The same procedures as of Example 1 were carried out except that the polymerization inhibitors as listed in Table 1 or Table 2 were used instead of the 4-hydroxy-2,2,6,6-tetramethylpiperidine-1-oxyl, the manganese acetate, and the maleic acid as the polymerization inhibitors. The results are listed in Table 1 or Table 2.

Comparative Examples 1 to 14

The same procedures as of Example 1 were carried out except that the polymerization inhibitors as listed in Table 3 or Table 4 were used instead of the 4-hydroxy-2,2,6,6-tetramethylpiperidine-1-oxyl, the manganese acetate, and the maleic acid as the polymerization inhibitors. The results are listed in Table 3 or Table 4.

TABLE 1

| | Polymerization inhibitor | Amount as added (weight %) | Formation time of polymerized product (hours) |
|---|---|---|---|
| Example 1 | 4-Hydroxy-2,2,6,6-tetramethylpiperidine-1-oxyl | 0.002 | 2.5 |
| | Manganese acetate | 0.002 | |
| | Maleic acid | 0.1 | |
| Example 2 | 4-Hydroxy-2,2,6,6-tetramethylpiperidine-1-oxyl | 0.002 | 2.0 |
| | Copper dibutyldithiocarbamate | 0.002 | |
| | Maleic acid | 0.1 | |

TABLE 1-continued

|  | Polymerization inhibitor | Amount as added (weight %) | Formation time of polymerized product (hours) |
| --- | --- | --- | --- |
| Example 3 | 4-Hydroxy-2,2,6,6-tetramethylpiperidine-1-oxyl | 0.002 | 2.0 |
|  | 4-Hydroxy-2,2,6,6-tetramethylpiperidine | 0.002 |  |
|  | Maleic acid | 0.1 |  |
| Example 4 | 4-Hydroxy-2,2,6,6-tetramethylpiperidine-1-oxyl | 0.002 | 2.5 |
|  | N-Nitroso-N-phenylhydroxylamine ammonium salt | 0.002 |  |
|  | Maleic acid | 0.1 |  |
| Example 5 | 4-Hydroxy-2,2,6,6-tetramethylpiperidine-1-oxyl | 0.002 | 2.5 |
|  | N-Nitroso-N-phenylhydroxylamine ammonium salt | 0.002 |  |
|  | Phthalic anhydride | 0.1 |  |
| Example 6 | 4-Hydroxy-2,2,6,6-tetramethylpiperidine-1-oxyl | 0.002 | 2.5 |
|  | N-Nitroso-N-phenylhydroxylamine ammonium salt | 0.002 |  |
|  | Acetic acid | 0.1 |  |
| Example 7 | 4-Hydroxy-2,2,6,6-tetramethylpiperidine-1-oxyl | 0.002 | 2.5 |
|  | N-Nitroso-N-phenylhydroxylamine ammonium salt | 0.002 |  |
|  | Salicylic acid | 0.1 |  |

TABLE 2

|  | Polymerization inhibitor | Amount as added (weight %) | Formation time of polymerized product (hours) |
| --- | --- | --- | --- |
| Example 8 | 4-Hydroxy-2,2,6,6-tetramethylpiperidine-1-oxyl | 0.001 | 2.0 |
|  | Manganese acetate | 0.001 |  |
|  | Copper dibutyldithiocarbamate | 0.001 |  |
|  | Maleic acid | 0.1 |  |
| Example 9 | 4-Hydroxy-2,2,6,6-tetramethylpiperidine-1-oxyl | 0.001 | 2.0 |
|  | Manganese acetate | 0.001 |  |
|  | 4-Hydroxy-2,2,6,6-tetramethylpiperidine | 0.001 |  |
|  | Maleic acid | 0.1 |  |
| Example 10 | 4-Hydroxy-2,2,6,6-tetramethylpiperidine-1-oxyl | 0.001 | 2.0 |
|  | Manganese acetate | 0.001 |  |
|  | N-Nitroso-N-phenylhydroxylamine ammnonium salt | 0.001 |  |
|  | Maleic acid | 0.1 |  |
| Example 11 | 4-Hydroxy-2,2,6,6-tetramethylpiperidine-1-oxyl | 0.001 | 1.8 |
|  | Copper dibutyldithiocarbamate | 0.001 |  |
|  | 4-Hydroxy-2,2,6,6-tetramethylpiperidine | 0.001 |  |
|  | Maleic acid | 0.1 |  |
| Example 12 | 4-Hydroxy-2,2,6,6-tetramethylpiperidine-1-oxyl | 0.001 | 2.0 |
|  | Copper dibutyldithiocarbamate | 0.001 |  |
|  | N-Nitroso-N-phenylhydroxylamine ammonium salt | 0.001 |  |
|  | Maleic acid | 0.1 |  |
| Example 13 | 4-Hydroxy-2,2,6,6-tetramethylpiperidine-1-oxyl | 0.001 | 2.0 |
|  | 4-Hydroxy-2,2,6,6-tetramethylpiperidine | 0.001 |  |
|  | N-Nitroso-N-phenylhydroxylamine ammonium salt | 0.001 |  |
|  | Maleic acid | 0.1 |  |

TABLE 3

|  | Polymerization inhibitor | Amount as added (weight %) | Formation time of polymerized product (hours) |
| --- | --- | --- | --- |
| Comparative Example 1 | 4-Hydroxy-2,2,6,6-tetramethylpiperidine-1-oxyl | 0.002 | 1.3 |
|  | Manganese acetate | 0.002 |  |
| Comparative Example 2 | 4-Hydroxy-2,2,6,6-tetramethylpiperidine-1-oxyl | 0.002 | 0.8 |
|  | Copper dibutyldithiocarbamate | 0.002 |  |
| Comparative Example 3 | 4-Hydroxy-2,2,6,6-tetramethylpiperidine-1-oxyl | 0.002 | 0.8 |
|  | 4-Hydroxy-2,2,6,6-tetramethylpiperidine | 0.002 |  |
| Comparative Example 4 | 4-Hydroxy-2,2,6,6-tetramethylpiperidine-1-oxyl | 0.002 | 1.0 |
|  | N-Nitroso-N-phenylhydroxylamine ammonium salt | 0.002 |  |
| Comparative Example 5 | Maleic acid | 0.1 | Not more than 0.5 |
| Comparative Example 6 | Phthalic anhydride | 0.1 | Not more than 0.5 |
| Comparative Example 7 | Acetic acid | 0.1 | Not more than 0.5 |
| Comparative Example 8 | Salicylic acid | 0.1 | Not more than 0.5 |

TABLE 4

| | Polymerization inhibitor | Amount as added (weight %) | Formation time of polymerized product (hours) |
|---|---|---|---|
| Comparative Example 9 | 4-Hydroxy-2,2,6,6-tetramethylpiperidine-1-oxyl | 0.001 | 1.0 |
| | Manganese acetate | 0.001 | |
| | Copper dibutyldithiocarbamate | 0.001 | |
| Comparative Example 10 | 4-Hydroxy-2,2,6,6-tetramethylpiperidine-1-oxyl | 0.001 | 1.0 |
| | Manganese acetate | 0.001 | |
| | 4-Hydroxy-2,2,6,6-tetramethylpiperidine | 0.001 | |
| Comparative Example 11 | 4-Hydroxy-2,2,6,6-tetramethylpiperidine-1-oxyl | 0.001 | 1.0 |
| | Manganese acetate | 0.001 | |
| | N-Nitroso-N-phenylhydroxylamine ammonium salt | 0.001 | |
| Comparative Example 12 | 4-Hydroxy-2,2,6,6-tetramethylpiperidine-1-oxyl | 0.001 | 0.8 |
| | Copper dibutyldithiocarbamate | 0.001 | |
| | 4-Hydroxy-2,2,6,6-tetramethylpiperidine | 0.001 | |
| Comparative Example 13 | 4-Hydroxy-2,2,6,6-tetramethylpiperidine-1-oxyl | 0.001 | 0.8 |
| | Copper dibutyldithiocarbamate | 0.001 | |
| | N-Nitroso-N-phenylhydroxylamine ammonium salt | 0.001 | |
| Comparative Example 14 | 4-Hydroxy-2,2,6,6-tetramethylpiperidine-1-oxyl | 0.001 | 0.8 |
| | 4-Hydroxy-2,2,6,6-tetramethylpiperidine | 0.001 | |
| | N-Nitroso-N-phenylhydroxylamine ammonium salt | 0.001 | |

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A process for inhibition of polymerization of a (meth)acrylate ester where (meth)acrylic acid is used as a raw material, and in which: an N-oxyl compound and at least one member selected from the group consisting of manganese salt compounds, copper salt compounds, 2,2,6,6-tetramethylpiperidine compounds, and nitroso compounds are used together as polymerization inhibitors, and further at least one acid selected from the group consisting off a carboxylic acid and a carboxylic anhydride is added to any place of all the steps of the production process for the (meth)acrylate ester, wherein the carboxylic acid or carboxylic anhydride is at least one member selected from the group consisting of oxalic acid, oxalic anhydride, malonic acid, succinic acid, succinic anhydride, fumaric acid, maleic acid, maleic anhydride, octanoic acid, adipic acid, sebacic acid, tetradecanedicarboxylic acid, 1,2,4-butanetricarboxylic acid, 1,3,6-hexanetricarboxylic acid, 1,2,3,4-butanetetracarboxylic acid, 1,2,3,4-pentanetetracarboxylic acid, 1,6,7,12-dodecanetetracarboxylic acid, benzoic acid, o-toluic acid, m-toluic acid, p-toluic acid, phthalic acid, phthalic anhydride, isophthalic acid, terephthalic acid, 2,6-naphthalenedicarboxylic acid, pyromellitic acid, pyromellitic anhydride, 1,2,4-benzenetricarboxylic acid, 1,4,5,8-naphthalenetetracarboxylic acid, 1,3,5,7-naphthalenetetracarboxylic acid, salicylic acid, and acetic acid.

2. A process according to claim 1, wherein the (meth)acrylate ester is a hydroxyalkyl (meth)acrylate.

3. The process according to claim 1, wherein the amount of the acid as added is 0.0001 to 1% by weight relative to the (meth)acrylate ester.

4. A process for inhibition of polymerization of a (meth)acrylate ester selected from the group consisting of methyl acrylate, ethyl acrylate, butyl acrylate, 2-ethylhexyl acrylate, hydroxyalkyl, acrylates, methyl methacrylate, butyl methacrylate, and hydroxyalkyl methacrylates where (meth)acrylic acid is used as a raw material, and in which: an N-oxyl compound and at least one member selected from the group consisting of manganese salt compounds, copper salt compounds, 2,2,6,6-tetramethylpiperidine compounds, and nitroso compounds are used together as polymerization inhibitors, and further at least one acid selected from the group consisting of a carboxylic acid and a carboxylic anhydride is added to any place of all the steps of the production process for the (meth)acrylate ester, wherein said carboxylic acid is a carboxylic acid other than (meth)acryiic acid.

5. A process according to claim 4, wherein the (meth)acrylate ester is a hydroxyalkyl (meth)acrylate.

6. A process according to claim 4, wherein the amount of the acid as added is 0.0001 to 1% by weight relative to the (meth)acrylate ester.

\* \* \* \* \*